(12) United States Patent
Komata et al.

(10) Patent No.: US 7,067,691 B2
(45) Date of Patent: Jun. 27, 2006

(54) PROCESS FOR PRODUCING α-SUBSTITUTED ACRYLIC ACID ESTERS

(75) Inventors: Takeo Komata, Saitama (JP); Kei Matsunaga, Saitama (JP); Yoshiki Hirotsu, Saitama (JP); Satoru Miyazawa, Saitama (JP); Katsunori Kawamura, Saitama (JP)

(73) Assignee: Central Glass Co., Ltd., Ube (JP)

( * ) Notice: Subject to any disclaimer, the term of this patent is extended or adjusted under 35 U.S.C. 154(b) by 0 days.

(21) Appl. No.: 11/016,770

(22) Filed: Dec. 21, 2004

(65) Prior Publication Data

US 2005/0165249 A1    Jul. 28, 2005

(30) Foreign Application Priority Data

Dec. 26, 2003    (JP)    ............... 2003-434390

(51) Int. Cl.
*C07C 69/62*    (2006.01)
*C07C 69/52*    (2006.01)

(52) U.S. Cl. ........................ 560/219; 560/223
(58) Field of Classification Search ............... None
See application file for complete search history.

(56) References Cited

U.S. PATENT DOCUMENTS

| | | | |
|---|---|---|---|
| 3,438,946 A * | 4/1969 | Lichstein et al. | ........... 528/299 |
| 3,662,071 A | 5/1972 | Langkammerer | |
| 4,859,793 A * | 8/1989 | Hurtel | ........................ 560/223 |
| 6,784,312 B1 | 8/2004 | Miyazawa et al. | |

2003/0224283 A1 *  12/2003  Allen et al. .............. 430/270.1

FOREIGN PATENT DOCUMENTS

JP    2003-040840    2/2003

OTHER PUBLICATIONS

Takashi Chiba et al., "157 nm Resist Materials: A Progress Report", Journal of Photopolymer Science and Technology, vol. 13, No. 4, 2000, p. 657.

* cited by examiner

*Primary Examiner*—Paul A. Zucker
(74) *Attorney, Agent, or Firm*—Crowell & Moring LLP

(57) ABSTRACT

A process for producing an α-substituted acrylic acid ester represented by the formula [1],

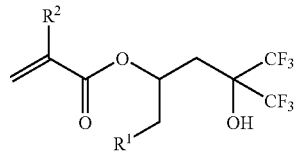

wherein each of $R^1$ and $R^2$ is independently a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group, includes reacting an α-substituted acrylic acid anhydride represented by the formula [7], with 1,1-bis(trifluoromethyl)-1,3-diol represented by the formula [2].

15 Claims, No Drawings

PROCESS FOR PRODUCING α-SUBSTITUTED ACRYLIC ACID ESTERS

BACKGROUND OF THE INVENTION

The present invention relates to a process for producing α-substituted acrylic acid esters, which are useful as monomers adapted to the next generation photoresists.

It is known that such α-substituted acrylic acid esters have bright prospects as monomers for the next generation resist materials and that such resists containing the monomers as their constituent element are superior in light transmission and surface adhesion (see U.S. Pat. No. 6,784,312 corresponding to Japanese Patent Laid-open Publication 2003-040840).

It is mentioned in U.S. Pat. No. 6,784,312 that an α, β-unsaturated ester is synthesized by reacting an alcohol with acrylic acid or acrylic chloride.

U.S. Pat. No. 3,662,071 discloses a process for synthesizing α-[(2-hydroxy-1-methyl-3,3,3-trifluoro-2-trifluoromethyl)propyl]benzyl alcohol by the steps of (a) heating hexafluoroacetone and propiophenone at 160° C.; and (b) reducing the product of the step (a) by aluminum isopropoxide using isopropanol as a solvent.

SUMMARY OF THE INVENTION

It is an object of the present invention to provide a process for producing an α-substituted acrylic acid ester, which is suitable for an industrial scale production.

According to the present invention, there is provided a first process for producing an α-substituted acrylic acid ester represented by the formula [1],

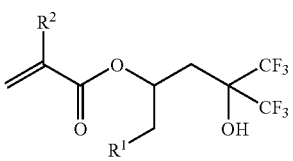

wherein each of $R^1$ and $R^2$ is independently a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group. This process comprises reacting an α-substituted acrylic acid anhydride represented by the formula [7],

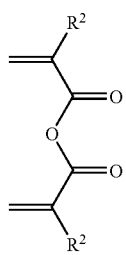

wherein $R^2$ is defined as above, with 1,1-bis(trifluoromethyl)-1,3-diol represented by the formula [2]

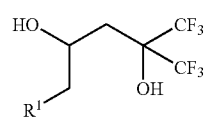

wherein $R^1$ is defined as above.

DETAILED DESCRIPTION

As mentioned above, U.S. Pat. No. 6,784,312 discloses a process for synthesizing compounds including the α-substituted acrylic acid ester represented by the formula [1]. In case that acrylic acid or acrylic chloride is used in this process (see the after-mentioned Comparative Examples 1 to 3 of the present application), it is necessary to conduct the reaction at a relatively high temperature of 95° C. or higher. Due to this, by-products are generated significantly, and thereby selectivity of the target product becomes low. As described in Comparative Example 3 of the present application, it is necessary to conduct the reaction for a long time as long as 47 hr under a heated condition at 110° C. in the case of using 2-methyl-2-butene as a deacidification agent. This also causes a significant production of by-products and thereby lowers selectivity of the target product.

Although U.S. Pat. No. 6,784,312 discloses a process for synthesizing compounds including the α-substituted acrylic acid ester represented by the formula [1], preferable reaction conditions are not disclosed therein.

As mentioned above, U.S. Pat. No. 3,662,071 discloses a process for synthesizing compounds including 1,1-bis(trifluoromethyl)-1,3-diol represented by the formula [2]. In this process, hexafluoroacetone and a ketone are heated at 160° C. without using catalyst. This causes a high pressure of about 4 MPa and therefore requires the use of a reaction apparatus proof against such high pressure. The product obtained by this heating is reduced by aluminum isopropoxide using isopropanol as a solvent. This causes a problem of the generation of wastes in large amounts such as the solvent and an organic waste water caused by the post-treatments.

In view of the above-mentioned problems of the prior art techniques, the present inventors have eagerly studied the process for producing an α-substituted acrylic acid ester represented by the formula [1], which is suitable for an industrial scale production. As a result, we have unexpectedly found that the target compound can much more mildly be produced, as compared with the process of U.S. Pat. No. 6,784,312, with high yield by the first process.

In particular, we have unexpectedly found that the α-substituted acrylic acid ester can be produced with high yield under a mild temperature condition of 0° C. to +80° C. by conducting the reaction in the presence of an additive. The production under such mild temperature condition is advantageous in suppressing the production of impurities that are difficult to be separated and in improving selectivity of the target product. The additive can be at least one acid selected from organic sulfonic acids (e.g., methanesulfonic acid, ethanesulfonic acid, p-toluenesulfonic acid, benzenesulfonic acid, and trifluoromethanesulfonic acid) and Lewis acids (e.g., $BF_3$, $BCl_3$, and anhydrous hydrogen fluoride).

Furthermore, we have found a second process for producing the above raw material 1,1-bis(trifluoromethyl)-1,3-diol, represented by the formula [2], comprising the steps of:

(a) reacting a fluorine-containing unsaturated alcohol represented by the formula [8],

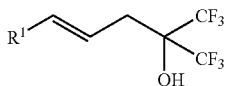

[8]

wherein $R^1$ is defined as above, with concentrated sulfuric acid, thereby producing a sulfuric ester; and (b) bringing the sulfuric ester into contact with water, thereby hydrolyzing the sulfuric ester into the 1,1-bis(trifluoromethyl)-1,3-diol. The second process can be conducted under normal pressure and mild condition. With this, the target compound 1,1-bis(trifluoromethyl)-1,3-diol can be obtained easily with high yield.

By conducting the second process and the first process in sequence, it becomes possible to advantageously produce the target compound, an α-substituted acrylic acid ester represented by the formula [1], by using a fluorine-containing unsaturated alcohol represented by the formula [8], which is relatively easily available for industrial use, as a starting material.

According to the present invention, it is possible by the first process (optionally combined with the second process) to effectively and selectively produce the target butyl ester. Thus, it is a superior process for producing the target butyl ester in an industrial scale.

The reaction scheme for conducting the second process and the first process in sequence can be summarized, as follows.

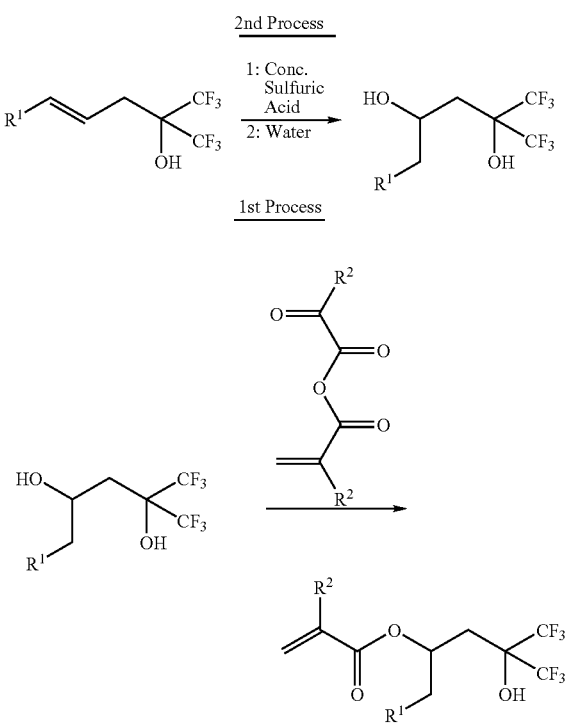

In view of the usefulness of the target butyl ester, it is preferable that $R^1$ is a hydrogen atom and $R^2$ is a hydrogen atom, methyl group, ethyl group, n-propyl group, isopropyl group, n-butyl group, sec-butyl group, tert-butyl group, or fluoromethyl group. It is particularly preferable that $R^1$ is a hydrogen atom and $R^2$ is a methyl group, or that each of $R^1$ and $R^2$ is a hydrogen atom, or that $R^1$ is a hydrogen atom and $R^2$ is a trifluoromethyl group.

It is possible to conduct each of the first and second processes by using a batch-wise reaction apparatus. The reaction conditions are exemplarily described in detail in the following. Certain modifications of the reaction conditions can be made by a person skilled in the art in respective reaction apparatuses.

Concentrated sulfuric acid used in the second process refers to a sulfuric acid having a concentration of not lower than about 80%, preferably not lower than 90%, more preferably not lower than 95%. It is thus possible to use a commercial concentrated sulfuric acid (e.g., 95% solution and 98% solution).

The fluorine-containing unsaturated alcohol, which is the raw material of the second process, can be synthesized, for example, by reacting a corresponding Grignard reagent with hexafluoroacetone (see J. Photopolym. Sci. Technol., Vol. 13, No. 4, 2000, p. 657).

The amount of concentrated sulfuric acid used in the second process may be 1.0 to 5.0 moles, preferably 1.0 to 4.0 moles, more preferably 1.0 to 3.0 moles, per mol of the fluorine-containing unsaturated alcohol. If it is less than 1.0 mole per that, selectivity of the reaction and yield of the target product may become inferior. If it is greater than 5.0 moles per that, the amount of concentrated sulfuric acid that is not involved in the reaction may become too much. This may not be preferable from the economical viewpoint.

The temperature range for conducting the reaction of the fluorine-containing unsaturated alcohol with concentrated sulfuric acid may be −30° C. to +100° C., preferably −20° C. to +80° C., more preferably −10° C. to +50° C. A temperature lower than −30° C. causes an excessive cooling. This is not economically preferable in terms of facility, energy and the like. If it is higher than +100° C., isomerization or decomposition of the fluorine-containing unsaturated alcohol may occur. Thus, this is not preferable.

In the second process, the amount of water used for hydrolyzing the sulfuric ester may be 1 to 100 moles, preferably 1 to 80 moles, more preferably 1 to 60 moles, per mole of the fluorine-containing unsaturated alcohol. If it is lower than 1 mole per that, the hydrolysis may not proceed sufficiently, and yield of the target product may thus become inferior. If it is greater than 100 moles per that, the amount of water that is not involved in the hydrolysis may become too much. This may cause disadvantage in operation (e.g., isolation of the target 1,1-bis(trifluoromethyl)-1,3-diol).

The hydrolysis of the second process may be conducted at a temperature of 0 to 200° C., preferably 20 to 150° C., more preferably 50 to 120° C. If it is lower than 0° C., the reaction rate may become too low as a practical production process. If it exceeds 200° C., the 1,1-bis(trifluoromethyl)-1,3-diol once produced may be decomposed.

In the hydrolysis, water and the unreacted concentrated sulfuric acid are brought into contact with each other. This may cause a strong heat generation. Therefore, it is preferable to conduct a certain operation (e.g., a gradual addition of the reaction mixture containing the sulfuric ester to water). It is thus preferable to conduct the temperature management by cooling the reactor with stirring.

The reaction time of the second process is not particularly limited. It is possible to suitably set the reaction time in order to sufficiently mix the reactants together and to sufficiently conduct the target reactions. For example, it is possible to conduct a stirring for about 2 hr after the temperature of the reaction liquid stabilizes following the mixing of the reagents.

The reaction vessel used in the second process may be made of a resin material (e.g., ethylene tetrafluoride resin, chlorotrifluoroethylene resin, vinylidene fluoride resin, and PFA resin). It may be one lined with glass or the like. Furthermore, it may be a glass vessel.

The 1,1-bis(trifluoromethyl)-1,3-diol obtained by the second process can be isolated by a normal liquid separation operation or by an extraction with organic solvent.

The first process is explained in detail, as follows. As mentioned above, the raw material of the first process, the 1,1-bis(trifluoromethyl)-1,3-diol represented by the formula [2], can be the product of the second process.

The α-substituted acrylic acid anhydride used in the first process may be 0.5 to 5.0 moles, preferably 0.7 to 3.0 moles, more preferably 1.0 to 2.0 moles, per mol of the 1,1-bis (trifluoromethyl)-1,3-diol. If it is less than 0.5 moles per that, conversion of the reaction and yield of the target product may become too low. If it exceeds 5.0 moles per that, the amount of the α-substituted acrylic acid anhydride that is not involved in the reaction may become too much. This increases a waste disposal load and thus is not preferable economically.

In the first process, it is possible to add an additive for accelerating the reaction. This additive may be at least one acid selected from organic sulfonic acids (e.g., methanesulfonic acid, ethanesulfonic acid, p-toluenesulfonic acid, benzenesulfonic acid, and trifluoromethanesulfonic acid) and Lewis acids (e.g., $BF_3$, $BCl_3$, and anhydrous hydrogen fluoride). Of these, organic sulfonic acids are preferable. In the case of adding the additive, its amount may be 0.01 to 2.0 moles, preferably 0.02 to 1.8 moles, more preferably 0.05 to 1.5 moles, per mol of the 1,1-bis(trifluoromethyl)-1,3-diol. If it is less than 0.01 moles per mol of that, conversion of the reaction and yield of the target product may become inferior. If it exceeds 2.0 moles per mol of that, the amount of the additive that is not involved in the reaction may become too much. Thus, this is not preferable.

In the case of not using the additive, the reaction temperature may be 80 to 200° C., preferably 100 to 180° C., more preferably 120 to 160° C. If it is lower than 80° C., the reaction rate may become too low. If it is higher than 200° C., the α-substituted acrylic acid anhydride (as the raw material) or butyl ester (as the product) may polymerize. In the case of adding the additive, the reaction temperature may be 0 to 80° C., preferably 10 to 70° C., more preferably 20 to 60° C. If it is lower than 0° C., the reaction rate may become too low as a practical process. If it is higher than 80° C., side reactions tend to occur. With this, the target butyl ester may become too low in selectivity. In the first process, it is preferable to add the additive, since the reaction can occur at a lower temperature and since selectivity can be improved. Thus, it is particularly preferable to conduct the reaction of the first process in the presence of the additive at a temperature of 20 to 60° C.

Although the reaction may proceed without using solvent, it is preferable to use a solvent in view of achieving reaction homogeneity and improving operability after the reaction. Examples of the solvent include aromatic compounds (e.g., benzene, toluene, xylene, and mesitylene), ethers (e.g., diethyl ether, methyl-tert-butyl ether, diisopropyl ether, and tetrahydrofuran), and halogen-containing compounds (e.g., methylene chloride, chloroform, and carbon tetrachloride). It is optional to use a single solvent or a mixture of solvents.

In the case of using a solvent, its amount may be 0.1 to 100 g, preferably 0.5 to 50 g, more preferably 1.0 to 20 g, per gram of the 1,1-bis(trifluoromethyl)-1,3-diol. If it is less than 0.1 g per gram of that, the merit of using solvent may not be sufficient. If it exceeds 100 g, it may be economically not preferable from the viewpoint of productivity.

It is optional and preferable to conduct the reaction in the presence of a polymerization inhibitor for the purpose of suppressing polymerization of the α-substituted acrylic acid anhydride or the α-substituted acrylic acid ester. The polymerization inhibitor may be at least one compound selected from hydroquinone, methoquinone, 2,5-di-t-butylhydroquinone, 1,2,4-trihydroxybenzene, 2,5-bistetramethylbutylhydroquinone, leucoquinizarin, phenothiazine, tetraethylthiuram, disulfide, 1,1-diphenyl-2-picrylhydrazyl, and 1,1-diphenyl-2-picrylhydrazine. Further examples of the polymerization inhibitor expressed in trade name, together with compound name in parenthesis, include NONFLEX F (N,N'-di-2-naphthyl-p-phenylenediamine), NONFLEX H (N,N'-diphenyl-p-phenylenediamine), NONFLEX DCD (4,4'-bis(α,α'-dimethyl benzyl)diphenylamine), NONFLEX MBP (2,2'-methylene-bis(4-methyl-6-tert-butylphenol), and OZONONE 35 (N-(1-methylheptyl)-N'-phenyl-p-phenylenediamine) of SEIKO CHEMICAL Co., Ltd located in Japan, and Q-1300 (N-nitrosophenylhydroxylamine ammonium salt) and Q-1301 (N-nitrosophenylhydroxylamine alminium salt) of Wako Pure Chemical Industries, Ltd. located in Japan. All of the above examples of the polymerization inhibitor are easily available as commercial products.

In the case of using a polymerization inhibitor in the reaction, its amount may be 0.00001 to 0.1 moles, preferably 0.0001 to 0.05 moles, more preferably 0.001 to 0.01 moles, per mol of the 1,1-bis(trifluoromethyl)-1,3-diol. Even if it exceeds 0.1 moles per mol of that, the effect of suppressing the polymerization may not improve further. Thus, this may be economically not preferable.

The reaction vessel used in the first process may be made of a resin material (e.g., ethylene tetrafluoride resin, chlorotrifluoroethylene resin, vinylidene fluoride resin, and PFA resin). It may be one lined with glass or the like. Furthermore, it may be a glass vessel or stainless steel vessel.

For example, the second process for producing the 1,1-bis(trifluoromethyl)-1,3-diol can be conducted, as follows. At first, concentrated sulfuric acid is put into a reactor that is proof against the reaction conditions. Then, the fluorine-containing unsaturated alcohol is added with stirring at a predetermined temperature and with cooling or heating from outside according to need. Then, the reaction is allowed to proceed at a predetermined temperature with stirring. The consumption of the raw material is monitored by sampling or the like. Once the raw material has been consumed, water is gradually added, followed by heating to a predetermined temperature. Once the termination of the reaction has been found by monitoring the consumption of the raw material, it is preferable to cool the reaction liquid down. The resulting 1,1-bis(trifluoromethyl)-1,3-diol can be purified by a normal conventional method. For example, the reaction liquid is extracted with a solvent (e.g., ether), followed by distilling the solvent off, thereby obtaining a crude organic matter. This organic matter can be subjected to a purification (e.g., column chromatography and distillation), thereby obtaining 1,1-bis(trifluoromethyl)-1,3-diol of high purity For example, the first process for producing the α-substituted acrylic acid ester can be conducted, as follows. At first, a reactor proof against the reaction conditions is charged with a solvent, the 1,1-bis(trifluoromethyl)-1,3-diol that may be one obtained by the second process, the α-substituted acrylic acid anhydride, a polymerization inhibitor, and an additive, followed by heating from outside with stirring to allow the reaction to proceed. It is possible to determine the termination of the reaction by monitoring the consumption of the raw material by sampling or the like. After that, it is preferable to cool the reaction liquid down. The resulting butyl ester can be purified by a normal purification method. For example, the reaction is treated with water, a sodium hydrogencarbonate aqueous solution, and then brine, followed by distilling the solvent out of the organic layer, thereby obtaining a crude organic matter. This crude organic matter can be purified by column chromatography, distillation or the like into the target butyl ester of high purity.

The following nonlimitative examples are illustrative of the present invention. Herein, the percent (%) of the compositional analysis value refers to areal % of an organic component (other than the solvent component) obtained by gas chromatography of a sampled reaction mixture that was extracted with diethyl ether or the like according to need.

EXAMPLE 1

(2nd Process)

A 1000 mL four-necked flask equipped with a dropping funnel, a reflux condenser and a thermometer was charged with a stirring magnet covered with tetrafluoroethylene resin and 141.3 g (1.44 mols) of concentrated sulfuric acid, followed by cooling in an iced water bath to 0–5° C. with stirring. Then, 151.2 g (0.72 mols) of 1,1,1-trifluoro-2-(trifluoromethyl)pent-4-en-2-ol were added dropwise from the dropping funnel. After the dropping, the temperature of the reaction mixture was raised to a temperature of 20 to 25° C. At this temperature, stirring was conducted for 2 hr. Then, 623.9 g (34.7 mols) of water were added, followed by heating to have an internal temperature of 90 to 95° C. with an oil bath. 2 hr later, the reaction liquid was found by gas chromatography to have a composition of 91.1% of the target 1,1-bis(trifluoromethyl)butane-1,3-diol, 2.3% of the raw material 1,1,1-trifluoro-2-(trifluoromethyl)pent-4-en-2-ol, and 6.6% of others. After cooling the reaction liquid down, it was extracted two times with 250 g of diisopropyl ether. The resulting solution was dried with 50 g of magnesium sulfate, followed by separating magnesium sulfate by filtration. The resulting filtrate was put into a distillation apparatus, followed by distilling diisopropyl ether off and then conducting a vacuum distillation under 35 Torr (4.67 kPa), thereby collecting a distillate having a boiling point range of 85 to 87° C. With this, 130.5 g of the target 1,1-bis(trifluoromethyl)butane-1,3-diol were obtained. Its composition was found by gas chromatography to be 100% of 1,1-bis(trifluoromethyl)butane-1,3-diol. The yield was 79.4%.

The NMR data of the product are as follows.

$^1$H NMR (solvent: CDCl$_3$; standard substance: TMS); δ 6.62 (s, 1H), 4.44 (m, 1H), 2.79 (d, J=3.90 Hz, 1H), 2.04 (m, 2H), 1.30 (d, J=6.0 Hz, 3H)

$^{19}$F NMR (solvent: CDCl$_3$; standard substance: CCl$_3$F); δ −76.2 (q, J=10.7 Hz, 3F), −80.0 (q, J=10.7 Hz, 3F)

EXAMPLE 2

(1st Process)

A 1000 mL three-necked flask equipped with a thermometer and a reflux condenser was charged with a stirring magnet covered with tetrafluoroethylene resin, 100.0 g (0.44 mols) of 1,1-bis(trifluoromethyl)butane-1,3-diol, 74.6 g (0.48 mols) of methacrylic acid anhydride, 4.23 g (0.044 mols) of methanesulfonic acid, 400 g of toluene, and 0.5 g of phenothiazine, followed by heating under reflux at 50° C. with an oil bath while the reaction mixture was stirred with a stirrer. 4 hr later, the reaction liquid was analyzed by gas chromatography. With this, it was found to have a composition (except methacrylic acid produced as a by-product) of 94.5% of 4,4,4-trifluoro-3-hydroxy-1-methyl-3-(trifluoromethyl)butyl 2-methacrylate, 1.6% of the raw material 1,1-bis(trifluoromethyl)butane-1,3-diol, 2.0% of methacrylic acid anhydride, and 1.9% of others.

The reaction liquid was washed two times with 200 g of water. The resulting organic layer was dried with 30 g of magnesium sulfate, followed by removing magnesium sulfate by filtration. Then, 0.7 g of phenothiazine as a polymerization inhibitor were added to the filtrate, followed by distilling the solvent off and then conducting a vacuum distillation under 8 Torr (1.07 kPa), thereby collecting a distillate having a boiling point range of 80 to 82° C. With this, 77.5 g of 4,4,4-trifluoro-3-hydroxy-1-methyl-3-(trifluoromethyl)butyl 2-methacrylate. It was found by gas chromatography to have a composition of 98.2% of 4,4,4-trifluoro-3-hydroxy-1-methyl-3-(trifluoromethyl)butyl 2-methacrylate, 0.2% of the raw material 1,1-bis(trifluoromethyl)butane-1,3-diol, and 1.6% of others. The yield was 58.8%.

The NMR data of the product are as follows.

$^1$H NMR (solvent: CDCl$_3$; standard substance: TMS); δ 6.16 (q, J=0.98 Hz, 1H), 5.96 (bs, 1H), 5.66 (q, J=1.46 Hz, 1H), 5.13–5.20 (m, 1H), 2.24–2.36 (m, 2H), 1.94 (dd, J=1.46 Hz, 0.98 Hz, 3H), 1.44 (d, J=6.34 Hz, 3H)

$^{19}$F NMR (solvent: CDCl$_3$; standard substance: CCl$_3$F); δ −77.03 (q, J=9.67 Hz, 3F), −79.25 (q, J=9.67 Hz, 3F)

It is understood from the results of Example 2 that the target product was obtained with high conversion and high selectivity using a mild temperature condition of 50° C. and that the production of by-products (others) was significantly lower than that of the following comparative examples.

Comparative Example 1

A 1000 mL four-necked flask equipped with a thermometer and a reflux condenser was charged with a stirring magnet covered with tetrafluoroethylene resin, 100.0 g (0.44 mols) of 1,1-bis(trifluoromethyl)butane-1,3-diol, 300 g of toluene, 58.7 g (0.48 mols) of 2,6-dimethylpyridine, 68.99 g (0.66 mols) of methacrylic chloride, and 0.5 g of NONFLEX MBP, followed by heating with an oil bath to have an internal temperature of 95 to 100° C. while the reaction mixture was stirred with a stirrer. 6 hr later, the reaction liquid was analyzed by gas chromatography. With this, it was found to have a composition of 89.0% of 4,4,4-trifluoro-3-hydroxy-1-methyl-3-(trifluoromethyl)butyl 2-methacrylate, 1.9% of the raw material 1,1-bis(trifluoromethyl)butane-1,3-diol, and 9.1% of others.

The NMR data of the product were the same as those of Example 2.

Comparative Example 2

A 1000 mL three-necked flask equipped with a thermometer, a quantitative water receiver and a reflux condenser was charged with a stirring magnet covered with tetrafluoroethylene resin, 100.0 g (0.44 mols) of 1,1-bis(trifluoromethyl)butane-1,3-diol, 45.5 g (0.53 mols) of methacrylic acid, 42.3 g (0.44 mols) of methanesulfonic acid, 400 g of toluene, and 0.5 g of phenothiazine, followed by heating at 120° C. under reflux with an oil bath while the reaction mixture was stirred with a stirrer. 6 hr later, about 8 mL of water produced by the reaction were separated by the quantitative water receiver. The reaction liquid was analyzed by gas chromatography. With this, it was found to have a composition of 92.4% of 4,4,4-trifluoro-3-hydroxy-1-methyl-3-(trifluoromethyl)butyl 2-methacrylate, 1.9% of the raw material 1,1-bis(trifluoromethyl)butane-1,3-diol, and 5.2% of others.

The NMR data of the product were the same as those of Example 2.

Comparative Example 3

A 500 mL four-necked flask equipped with a reflux condenser was charged with a stirring magnet covered with tetrafluoroethylene resin, 60.03 g (0.265 mols) of 1,1-bis(trifluoromethyl)butane-1,3-diol, 230 g of toluene, 37.24 g (0.531 mols) of 2-methyl-2-butene, 0.30 g of NONFLEX MBP, and 36.04 g (0.398 mols) of acrylic chloride, followed by heating at 110° C. under reflux with an oil bath while the reaction mixture was stirred with a stirrer. 47 hr later, the reaction liquid was analyzed by gas chromatography. With this, it was found to have a composition of 87.6% of 4,4,4-trifluoro-3-hydroxy-1-methyl-3-(trifluoromethyl)butyl acrylate, 1.0% of the raw material 1,1-bis(trifluoromethyl)butane-1,3-diol, and 11.4% of others. The reaction liquid was cooled down to room temperature, followed by adding 100 g of water in a dropwise manner. The resulting organic layer was separated from the aqueous layer.

The NMR data of the product were as follows.
$^1$H NMR (solvent: CDCl$_3$; standard substance: TMS); δ 6.48 (1H, dd, J=17.2 Hz, 1.2Hz), 6.11 (1H, dd, J=17.2 Hz, 10.4 Hz), 5.94 (1H, dd, J=10.4 Hz, 1.2 Hz), 5.83 (1H, bs), 5.22–5.13 (1H, m), 2.36–2.23 (2H, m), 1.44 (1H, d, J=6.4 Hz)
$^{19}$F NMR (solvent: CDCl$_3$; standard substance: CCl$_3$F); δ −77.0 (3F, q, J=12.4 Hz), −79.4 (3F, q, J=12.4 Hz)

Comparative Example 4

A 1000 mL three-necked flask equipped with a thermometer and a reflux condenser was charged with a stirring magnet covered with tetrafluoroethylene resin, 150 g (0.66 mols) of 1,1-bis(trifluoromethyl)butane-1,3-diol, 126.9 g (0.80 mols) of 2-trifluoromethylacrylic chloride, 78.3 g (0.73 mols) of 2,6-dimethylpyridine, 260 g of toluene, and 0.75 g of NONFLEX MBP, followed by heating at 50° C. with an oil bath while the reaction mixture was stirred with a stirrer. 2 hr later, the reaction liquid was analyzed by gas chromatography. With this, it was found to have a composition of 85.7% of 4,4,4-trifluoro-3-hydroxy-1-methyl-3-(trifluoromethyl)butyl 2-(trifluoromethyl)acrylate, 2.1% of the raw material 1,1-bis(trifluoromethyl)butane-1,3-diol, and 12.2% of others.

The NMR data of the product were as follows.
$^1$H NMR (solvent: CDCl$_3$; standard substance: TMS); δ 6.79 (d, J=1.46 Hz, 1H), 6.51 (d, J=1.46 Hz, 1H), 5.33–5.40 (m, 1H), 4.65 (bs, 1H), 2.25–2.42 (m, 2H), 1.46 (d, J=6.34 Hz, 3h)
$^{19}$F NMR (solvent: CDCl$_3$; standard substance: CCl$_3$F); δ −65.92 (s, 3F), −77.20 (q, J=9.66 Hz, 3F), −79.09 (q, J=9.66 Hz, 3F)

Each of Comparative Examples 1 to 4 was lower than Example 2 in selectivity of the target product at the end of the reaction and was greater than Example 2 in the production of impurities (others) not having a particular structure.

What is claimed is:

1. A process for producing an α-substituted acrylic acid ester represented by the formula [1],

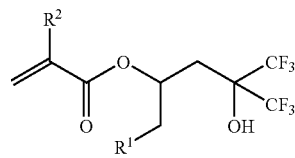

wherein each of R$^1$ and R$^2$ is independently a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group, the process comprising reacting an α-substituted acrylic acid anhydride represented by the formula [7],

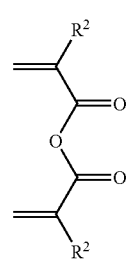

wherein R$^2$ is defined as above, with 1,1-bis(trifluoromethyl)-1,3-diol represented by the formula [2]

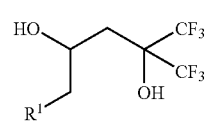

wherein R$^1$ is defined as above,
wherein the 1,1-bis(trifluoromethyl)-1,3-diol is obtained by a process comprising the steps of:
(a) reacting a fluorine-containing unsaturated alcohol represented by the formula [8].

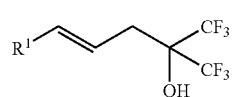

wherein R$^1$ is defined as in the formula [1], with concentrated sulfuric acid, thereby producing a sulfuric ester; and
(b) bringing the sulfuric ester into contact with water, thereby hydrolyzing the sulfuric ester into the 1,1-bis(trifluoromethyl)-1,3-diol.

2. A process according to claim 1, wherein R$^1$ is a hydrogen atom, and R$^2$ is a hydrogen atom, methyl group, ethyl group, n-propyl group, isopropyl group, n-butyl group, sec-butyl group, tert-butyl group, or fluoromethyl group.

3. A process according to claim 1, wherein R¹ is a hydrogen atom, and R² is a methyl group.

4. A process according to claim 1, wherein each of R¹ and R² is a hydrogen atom.

5. A process according to claim 1, wherein R¹ is a hydrogen atom, and R² is a trifluoromethyl group.

6. A process according to claim 1, wherein the reaction is conducted in the presence of at least one additive that is an organic sulfonic acid or Lewis acid.

7. A process according to claim 6, wherein the at least one additive is an organic sulfonic acid.

8. A process according to claim 7, wherein the organic sulfonic acid is selected from the group consisting of methanesulfonic acid, ethanesulfonic acid, p-toluenesulfonic acid, benzenesulfonic acid, and trifluoromethanesulfonic acid.

9. A process for producing an α-substituted acrylic acid ester represented by the formula [1],

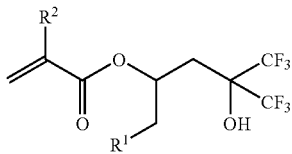

[1]

wherein each of R¹ and R² is independently a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group, the process comprising reacting an α-substituted acrylic acid anhydride represented by the formula [7],

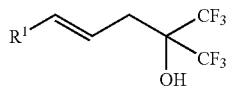

[8]

wherein R² is defined as above, with 1,1-bis(trifluoromethyl)-1,3-diol represented by the formula [2]

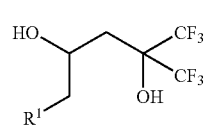

[2]

wherein R¹ is defined as above, wherein the reaction is conducted in the presence of at least one additive that is a Lewis acid, and wherein the Lewis acid is selected from the group consisting of BF₃, BCl₃, and anhydrous hydrogen fluoride.

10. A process according to claim 9, wherein the reaction is conducted at a temperature of 0° C. to 80° C.

11. A process according to claim 9, wherein the reaction is conducted in a solvent.

12. A process according to claim 11, wherein the solvent is at least one selected from the group consisting of aromatic compounds, ethers, and halogen-containing compounds.

13. A process according to claim 12, wherein the aromatic compounds are benzene, toluene, xylene and mesitylene, the ethers are diethyl ether, methyl-tert-butyl ether, diisopropyl ether and tetrahydrofuran, and the halogen-containing compounds are methylene chloride, chloroform, and carbon tetrachloride.

14. A process according to claim 1, wherein the reaction is conducted in the presence of a polymerization inhibitor.

15. A process according to claim 14, wherein the polymerization inhibitor is at least one compound selected from the group consisting of hydroquinone, methoquinone, 2,5-di-t-butylhydroquinone, 1,2,4-trihydroxybenzene, 2,5-bistetramethylbutylhydroquinone, leucoquinizarin, N,N'-di-2-naphthyl-p-phenylenediamine, N,N'-diphenyl-p-phenylenediamine, 4,4'-bis(α,α'-dimethyl benzyl) diphenylamine, 2,2'-methylene-bis(4-methyl-6-tert-butylphenol), N-(1-methylheptyl) -N'-phenyl-p-phenylenediamine, phenothiazine, tetraethylthiuram, disulfide, 1,1-diphenyl-2-picrylhydrazyl, 1,1-diphenyl-2-picrylhydrazine, N-nitrosophenylhydroxylamine ammonium salt, and N-nitrosophenylhydroxylamine aluminum salt.

* * * * *